(12) United States Patent
Shameli et al.

(10) Patent No.: US 12,011,213 B2
(45) Date of Patent: Jun. 18, 2024

(54) SYSTEM AND METHOD FOR TREATING EPISTAXIS

(71) Applicants: Acclarent, Inc., Irvine, CA (US);
Biosense Webster (Israel) Ltd, Yokneam (IL)

(72) Inventors: Ehsan Shameli, Irvine, CA (US); Fatemeh Akbarian, Rancho Palos Verdes, CA (US); Assaf Govari, Haifa (IL); Yehuda Algawi, Binyamina (IL)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 598 days.

(21) Appl. No.: 16/745,469

(22) Filed: Jan. 17, 2020

(65) Prior Publication Data

US 2020/0305969 A1    Oct. 1, 2020

Related U.S. Application Data

(60) Provisional application No. 62/825,941, filed on Mar. 29, 2019.

(51) Int. Cl.
*A61B 18/14* (2006.01)
*A61B 1/018* (2006.01)
(Continued)

(52) U.S. Cl.
CPC .......... *A61B 18/1492* (2013.01); *A61B 1/018* (2013.01); *A61B 1/233* (2013.01);
(Continued)

(58) Field of Classification Search
CPC ..... A61B 18/1492; A61B 34/20; A61B 1/018; A61B 1/233; A61B 2018/00327;
(Continued)

(56) References Cited

U.S. PATENT DOCUMENTS

| 5,078,716 A | 1/1992 | Doll |
| 5,733,282 A | 3/1998 | Ellman et al. |

(Continued)

FOREIGN PATENT DOCUMENTS

| CN | 1222843 A | 4/1999 |
| CN | 1224338 A | 7/1999 |

(Continued)

OTHER PUBLICATIONS

Kosugi, Breaking paradigms in severe epistaxis: the importance of looking for the S-point, Jan. 20, 2018, Brazilian Journal of Otorhinolaryngology, 84(3):p. 290-297 (Year: 2018).*

(Continued)

*Primary Examiner* — Michael F Peffley
*Assistant Examiner* — Bo Ouyang
(74) *Attorney, Agent, or Firm* — Frost Brown Todd LLP (57) ABSTRACT

A method of treating epistaxis includes inserting a distal end of an endoscope into a nasal cavity of a patient. At least the distal end of the endoscope includes a working channel. The method includes advancing a distal end of an RF ablation catheter through the working channel of the endoscope. The method also includes ablating tissue in a posterior nasal region of the nasal cavity using RF energy transmitted by the RF ablation catheter.

18 Claims, 8 Drawing Sheets

(51) Int. Cl.
*A61B 1/233* (2006.01)
*A61B 34/20* (2016.01)
*A61B 18/00* (2006.01)
*A61B 18/12* (2006.01)

(52) U.S. Cl.
CPC .... *A61B 34/20* (2016.02); *A61B 2018/00327* (2013.01); *A61B 2018/00577* (2013.01); *A61B 2018/00982* (2013.01); *A61B 2018/126* (2013.01); *A61B 2034/2057* (2016.02)

(58) Field of Classification Search
CPC .......... A61B 2018/00577; A61B 2018/00982; A61B 2018/126; A61B 2034/2057
See application file for complete search history.

(56) References Cited

U.S. PATENT DOCUMENTS

| | | | |
|---|---|---|---|
| 6,045,549 A | 4/2000 | Smethers, II | |
| 6,109,268 A | 8/2000 | Thapliyal et al. | |
| 6,139,545 A | 10/2000 | Utley et al. | |
| 6,210,355 B1 | 4/2001 | Edwards et al. | |
| 6,361,531 B1 | 3/2002 | Hissong | |
| 6,416,512 B1 | 7/2002 | Ellman et al. | |
| 6,447,510 B1 | 9/2002 | Ellman et al. | |
| 6,526,318 B1 | 3/2003 | Ansarinia | |
| 6,562,036 B1 | 5/2003 | Ellman et al. | |
| 6,572,613 B1 | 6/2003 | Ellman et al. | |
| 6,911,027 B1 | 6/2005 | Edwards et al. | |
| 6,920,883 B2 | 7/2005 | Bessette et al. | |
| 7,001,380 B2 | 2/2006 | Goble | |
| 7,004,941 B2 | 2/2006 | Tvinnereim et al. | |
| 7,297,143 B2 | 11/2007 | Woloszko et al. | |
| 7,377,918 B2 | 5/2008 | Amoah | |
| 7,491,200 B2 | 2/2009 | Underwood | |
| 7,720,521 B2 | 5/2010 | Chang et al. | |
| 7,842,034 B2 | 11/2010 | Mittelstein et al. | |
| 7,862,560 B2 | 1/2011 | Marion | |
| 7,892,230 B2 | 2/2011 | Woloszko | |
| 8,290,582 B2 | 10/2012 | Lin et al. | |
| 8,298,243 B2 | 10/2012 | Carlton et al. | |
| 8,512,335 B2 | 8/2013 | Cheng et al. | |
| 8,747,401 B2 | 6/2014 | Gonzalez et al. | |
| 8,900,227 B2 | 12/2014 | Stierman | |
| 8,936,594 B2 | 1/2015 | Wolf et al. | |
| 8,961,510 B2 | 2/2015 | Alshemari | |
| 8,979,842 B2 | 3/2015 | McNall, III et al. | |
| 9,011,428 B2 | 4/2015 | Nguyen et al. | |
| 9,072,597 B2 | 7/2015 | Wolf et al. | |
| 9,393,067 B2 | 7/2016 | van der Burg | |
| 9,415,194 B2 | 8/2016 | Wolf et al. | |
| 9,474,915 B2 | 10/2016 | Gonzales et al. | |
| 9,532,796 B2 | 1/2017 | DuBois et al. | |
| 9,649,144 B2 | 5/2017 | Aluru et al. | |
| 9,687,288 B2 | 6/2017 | Saadat | |
| 10,028,781 B2 | 7/2018 | Saadat | |
| 10,463,242 B2 | 11/2019 | Kesten et al. | |
| 2003/0208250 A1 | 11/2003 | Edwards et al. | |
| 2004/0204747 A1 | 10/2004 | Kemeny et al. | |
| 2005/0020901 A1* | 1/2005 | Belson .............. G02B 23/2476 | |
| | | | 600/407 |
| 2005/0240147 A1 | 10/2005 | Makower et al. | |
| 2005/0283148 A1 | 12/2005 | Janssen et al. | |
| 2006/0004323 A1 | 1/2006 | Chang et al. | |
| 2006/0052776 A1 | 3/2006 | Desinger et al. | |
| 2006/0069303 A1* | 3/2006 | Couvillon .......... A61B 18/1492 | |
| | | | 600/129 |
| 2006/0178670 A1 | 8/2006 | Woloszko et al. | |
| 2007/0027451 A1 | 2/2007 | Desinger et al. | |
| 2007/0073282 A1 | 3/2007 | McGaffigan et al. | |
| 2008/0027423 A1 | 1/2008 | Choi et al. | |
| 2008/0027505 A1 | 1/2008 | Levin et al. | |
| 2010/0274164 A1 | 10/2010 | Juto | |
| 2011/0160740 A1 | 6/2011 | Makower et al. | |
| 2012/0029498 A1 | 2/2012 | Branovan | |
| 2012/0101494 A1 | 4/2012 | Cadouri et al. | |
| 2012/0184954 A1* | 7/2012 | Onishi .............. A61B 18/1492 | |
| | | | 606/41 |
| 2012/0191089 A1* | 7/2012 | Gonzalez ........... A61B 18/1485 | |
| | | | 606/41 |
| 2012/0316557 A1 | 12/2012 | Sartor et al. | |
| 2014/0100557 A1 | 4/2014 | Bohner et al. | |
| 2014/0324037 A1 | 10/2014 | Hoey et al. | |
| 2014/0364725 A1 | 12/2014 | Makower | |
| 2015/0150624 A1 | 6/2015 | Petersohn | |
| 2016/0008083 A1 | 1/2016 | Kesten et al. | |
| 2016/0058495 A1 | 3/2016 | Twomey | |
| 2016/0058500 A1 | 3/2016 | Sharp et al. | |
| 2016/0256181 A1 | 9/2016 | Allen, IV et al. | |
| 2016/0324531 A1* | 11/2016 | Gross .................. A61B 18/148 | |
| 2016/0331459 A1* | 11/2016 | Townley ............... A61N 5/022 | |
| 2017/0165459 A1 | 6/2017 | Gross et al. | |
| 2017/0197075 A1 | 7/2017 | Van Bruggen et al. | |
| 2017/0231474 A1 | 8/2017 | Saadat et al. | |
| 2018/0078327 A1 | 3/2018 | Lin et al. | |
| 2018/0103994 A1 | 4/2018 | Fox et al. | |
| 2018/0116711 A1 | 5/2018 | Suh | |
| 2018/0133460 A1 | 5/2018 | Townley et al. | |
| 2018/0177541 A1 | 6/2018 | Regadas | |
| 2018/0177546 A1 | 6/2018 | Dinger et al. | |
| 2018/0193052 A1 | 7/2018 | Govari et al. | |
| 2018/0228533 A1 | 8/2018 | Wolf et al. | |
| 2018/0263678 A1 | 9/2018 | Saadat | |
| 2018/0310886 A1 | 11/2018 | Salazar et al. | |

FOREIGN PATENT DOCUMENTS

| | | |
|---|---|---|
| EP | 1049413 A1 | 11/2000 |
| EP | 1189543 A1 | 3/2002 |
| EP | 1416870 A4 | 5/2004 |
| EP | 3027133 A4 | 6/2016 |
| EP | 3030183 A1 | 6/2016 |
| EP | 3157454 B1 | 4/2017 |
| EP | 3258864 A1 | 12/2017 |
| WO | WO 1999/003411 A1 | 1/1999 |
| WO | WO 1999/030655 A1 | 6/1999 |
| WO | WO 2001/012089 A1 | 2/2001 |
| WO | WO 2008/079476 A2 | 7/2008 |
| WO | WO 2011/005903 A2 | 1/2011 |
| WO | WO 2011/025830 A1 | 3/2011 |
| WO | WO 2018/075273 A1 | 4/2018 |

OTHER PUBLICATIONS

Fukutake, Tomoshige, et al. "Laser surgery for allergic rhinitis." *Archives of Otolaryngology-Head & Neck Surgery* 112.12 (1986): 1280-1282.
Gindros, George, et al. "Mucosal changes in chronic hypertrophic rhinitis after surgical turbinate reduction." *European archives of oto-rhino-laryngology* 266.9 (2009):1409-1416.
Ho, Ki-Hong Kevin, et al. "Electromechanical reshaping of septal cartilage." *The Laryngoscope* 113.11 (2003): 1916-1921.
International Search Report and Written Opinion dated Jun. 8, 2020 for International Application No. PCT/IB2020/052648, 17 pages.

* cited by examiner

SYSTEM AND METHOD FOR TREATING EPISTAXIS

PRIORITY

This application claims priority to U.S. Provisional Patent App. No. 62/825,941, entitled "System and Method for Treating Epistaxis," filed Mar. 29, 2019, the disclosure of which is incorporated by reference herein.

BACKGROUND

Epistaxis is acute hemorrhage in the nostril, nasal cavity, or nasopharynx. Epistaxis may cause significant anxiety in patients and clinicians. Generally, epistaxis occurs in the anterior part of the nose, with the bleeding usually arising from the rich arterial anastomoses of the nasal septum (Kiesselbach's plexus). Posterior epistaxis generally arises from the posterior nasal region via branches of the sphenopalatine arteries. Such bleeding may occur behind the posterior portion of the middle turbinate or at the posterior superior roof of the nasal cavity.

While several systems and methods have been made and used to treat epistaxis, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is, by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. First Exemplary System

Figure 1:
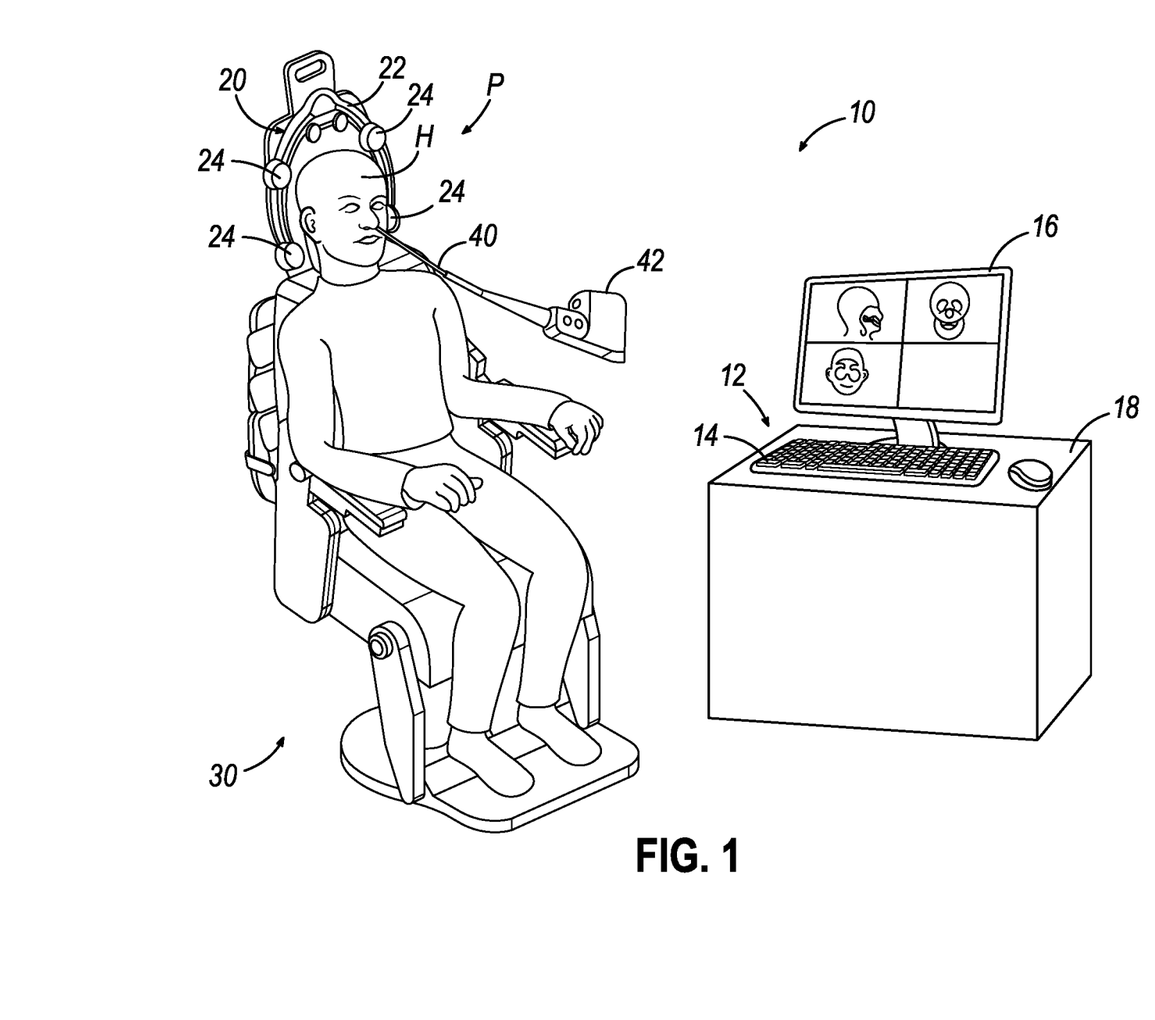
FIG. 1 depicts a schematic view of an exemplary system being used on a patient seated in an exemplary medical procedure chair.

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary system (10), e.g. an Image Guided Surgery (IGS) navigation system, enabling an ENT procedure to be performed using image guidance. In addition to or in lieu of having the components and operability described herein, system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

System (10) of the present example comprises a field generator assembly (20), which comprises a set of magnetic field generators (24) that are integrated into a horseshoe-shaped frame (22). Field generators (24) are operable to generate alternating magnetic fields of different frequencies around the head (H) of the patient (P). An endoscope (40) is inserted into the head (H) of the patient (P) in this example. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pub. No. 2018/0310886, entitled "Apparatus to Secure Field Generating Device to Chair," published Nov. 1, 2018, the disclosure of which is incorporated by reference herein.

System (10) of the present example further comprises a processor (12), which controls field generators (24) and other elements of system (10). For instance, processor (12) is operable to drive field generators (24) to generate alternating electromagnetic fields and process signals from endoscope (40) to determine the location of a position sensor (not shown) in endoscope (40) within the head (H) of the patient (P). Processor (12) comprises a processing unit communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Endoscope (40) includes a position sensor that is responsive to positioning within the alternating magnetic fields generated by field generators (24). A coupling unit (42) is secured to the proximal end of endoscope (40) and is configured to provide communication of data and other signals between console (18) and endoscope (40). Coupling unit (42) may provide wired or wireless communication of data and other signals.

In the present example, position sensor of endoscope (40) comprises at least one coil at the distal end (48) of endoscope (40). When such a coil is positioned within an alternating electromagnetic field generated by field generators (24), the alternating magnetic field may generate electrical current in the coil, and this electrical current may be communicated along the electrical conduit(s) in endoscope (40) and further to processor (12) via coupling unit (42). This phenomenon may enable system (10) to determine the location of distal end (48) of endoscope (40) within a three-dimensional space (i.e., within the head (H) of the patient (P), etc.). To accomplish this, processor (12) executes an algorithm to calculate location coordinates of distal end (48) of endoscope (40) from the position-related signals of the coil(s) in position sensor of endoscope (40).

Processor (12) uses software stored in a memory of processor (12) to calibrate and operate system (10). Such operation includes driving field generators (24), processing data from endoscope (40), processing data from operating controls (14), and driving display screen (16). In some implementations, operation may also include monitoring and enforcement of one or more safety features or functions of IGS navigation system (10). Processor (12) is further operable to provide video in real time via display screen (16), showing the position of distal end (48) of endoscope (40) in relation to a video camera image of the patient's head (H), a CT scan image of the patient's head (H), and/or a computer-generated three-dimensional model of the anatomy within and adjacent to the patient's nasal cavity. Display screen (16) may display such images simultaneously and/or superimposed on each other during the surgical procedure. Such displayed images may also include graphical representations endoscope (40) in the patient's head (H), such that the operator may view the virtual rendering of endoscope (40) at its actual location in real time. By way of example only, display screen (16) may provide images in accordance with at least some of the teachings of U.S. Pub. No. 2016/0008083, entitled "Guidewire Navigation for Sinuplasty," published Jan. 14, 2016, now U.S. Pat. No. 10,463,242, issued Nov. 5, 2019, the disclosure of which is incorporated by reference herein. Endoscopic images that are being captured by endoscope (40), as described below, may also be provided on display screen (16).

The images provided through display screen (16) may help guide the operator in maneuvering and otherwise manipulating endoscope (40) within the patient's head (H). It should also be understood that various other kinds of surgical instruments (e.g., guidewires, guide catheters, dilation catheters, suction instruments, shaver instruments, etc.) may incorporate a position sensor like position sensor of endoscope (40). As described above, in the context of endoscope (40), system (10) may enable an operator to view the position of the sensor-equipped instrument within the head (H) of the patient (P) in real time, such as by superimposing a position indicator on dynamically-changing views from a set of preoperatively obtained images (e.g., CT scans, etc.) of the head (H) of the patient (P).

II. Second Exemplary System

Severe epistaxis, also called acute epistaxis, may be less common than general epistaxis but is potentially life-threatening and may require urgent treatment. The Stamm's S-point region of the posterior nasal region may be the source of bleeding in severe epistaxis. However, the Stamm's S-point region is difficult to access, since the Stamm's S-point region is posterior to the septal body. In addition, bleeding may be significant enough to reach the lateral nasal wall and flow posteriorly, and, as a result, the bleeding may be mistakenly identified as posterior epistaxis. Consequently, severe epistaxis originating from the Stamm's S-point region may not be diagnosed correctly, which may lead to therapeutic failures. In addition, for other types of epistaxis, endoscopic access remains to be a challenge for treatment of posterior epistaxis originating from posterior aspects of the nasal cavity.

The nasal cavity (e.g. the posterior nasal region) is a relatively small space with various tortuous pathways and obstacles. Thus, in order to maximize access for an instrument within the nasal cavity, it is advantageous to provide such an instrument with a relatively small form factor and at least some degree of flexibility as will be described below. It may be further beneficial to provide such an instrument with steerability, such that the operator may actively bend or otherwise move the distal portion of the instrument relative to the proximal portion of the instrument, thereby allowing the distal portion of the instrument to more actively maneuver around anatomical structures to reach spaces that would otherwise be inaccessible to a fully-rigid instrument. As a result, it would be desirable to improve to provide a system that assists with these and other problems.

As will be described in reference to the following figures, an exemplary system (110) includes an endoscope (112), an RF ablation catheter (114), an RF energy source (116), and a control (118). RF energy source (116) is configured to provide radiofrequency (RF) energy to RF ablation catheter (114) to ablate tissue in a posterior nasal region of the nasal cavity.

A. Exemplary Endoscope

Figure 2A:
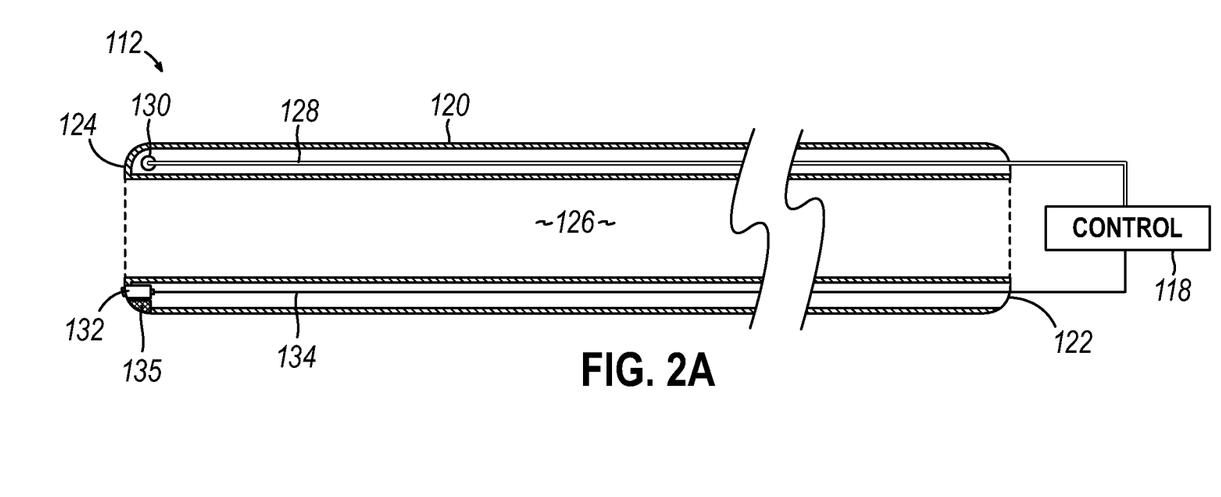
FIG. 2A depicts a side sectional view of an exemplary endoscope, similar to the endoscope of FIG. 1, in a straight configuration.
Figure 2B:
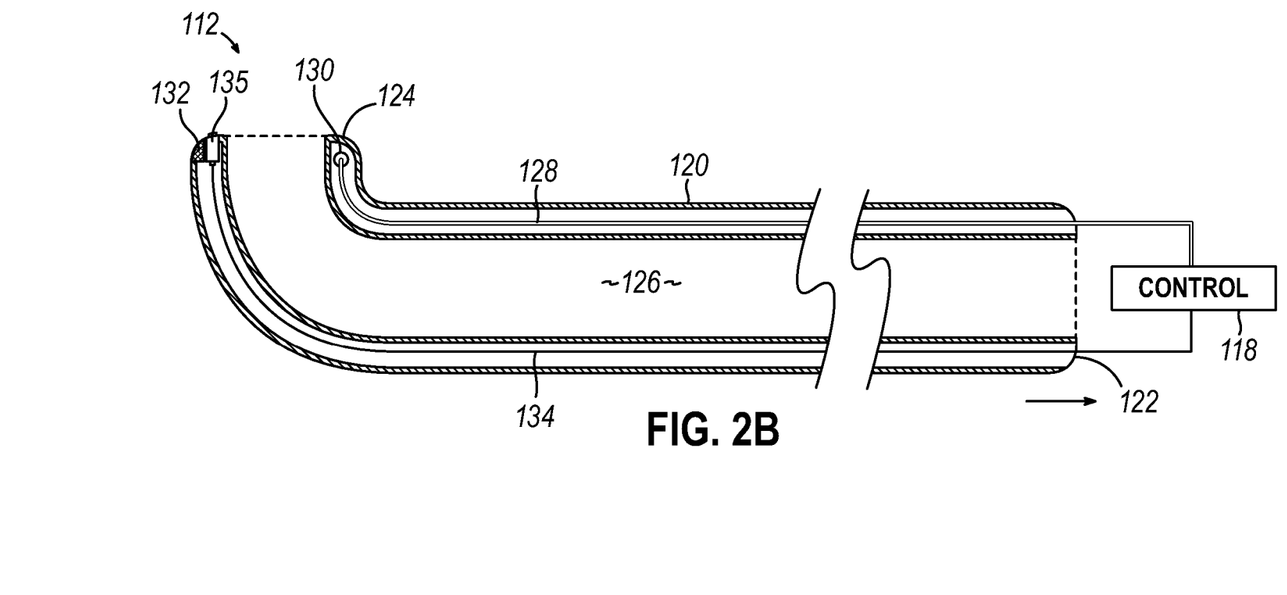
FIG. 2B depicts a side sectional view of the endoscope of FIG. 2A, but with a pull wire retracted proximally to articulate the distal end of the endoscope to a bent configuration.

FIGS. 2A-2B show endoscope (112), which may be similar to endoscope (40) described and shown above with reference to FIG. 1. Endoscope (112) includes a shaft (120) defining a longitudinal axis (LA). Shaft (120) includes a proximal end (122) and a distal end (124) disposed opposite proximal end (122). Endoscope (112) includes a working channel (126) that extends at least though distal end (124). As shown, working channel (126) extends completely through the entire length of endoscope (112) between and through both proximal and distal ends (122, 124). However, it is also envisioned that working channel (126) may extend only partially through shaft (120), such that working channel (126) terminates at a lateral side of shaft (120). As will be described in greater detail with reference to FIG. 4A, distal end (124) of shaft (120) is sized and configured to fit through nostril (N) of patient (P) and into nasal cavity (NC).

As shown in FIGS. 2A-2B, endoscope (112) includes at least one pull wire (128) attached at a distal attachment point (130) of shaft (120). As shown, pull wire (128) terminates just prior to distal end (124) of shaft (120) and may be attached to shaft (120) using a variety of different attachment structures (e.g. adhesive, welds, fasteners). Particularly, FIG. 2A shows a side sectional view of distal end (124) in a straight configuration, while FIG. 2B shows a side sectional view of distal end (124) in a bent configuration. The bent, or articulated, configuration may be obtained by proximally retracting a pull wire (128) using control (118). As such, some or all of shaft (120) may be flexible to aid in this bending.

Control (118) may include features that control articulation, provide entry into working channel (126), and/or couple with a visualization system (e.g. Image Guided Surgery (IGS) navigation system). For example, control (118) may include a display screen (not shown), similar to display screen (16) of FIG. 1. As shown, endoscope (112) includes a camera (132) at distal end (124) of endoscope (112). Camera (132) is configured to produce images which control (118) displays on the display screen (e.g. display screen (16)) to ensure proper positioning of RF ablation catheter (114). Camera (132) may communicate with control (118) using a wired connection (shown as camera cable (134)) or a wireless connection. As such, prior to ablating tissue in posterior nasal region (PNR), the position of endoscope (112) and/or RF ablation catheter (114) may be verified to ensure proper positioning in posterior nasal region (PNR) using images provided by camera (132) on the display screen. Endoscope (112) may include a position sensor (135) similar to the position sensor of endoscope (40). As a result, system (110) may track the position of distal end (124) of endoscope (112), based on signals from position sensor (135). The sensor data may thus supplement, or even substitute, the position feedback provided by visualization through camera (132).

B. Exemplary RF Ablation Catheter

Figure 3:
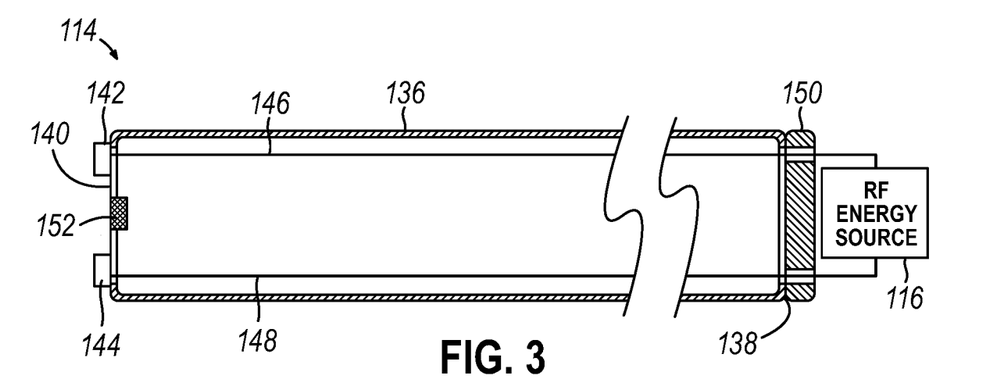
FIG. 3 depicts a side sectional view of an exemplary RF ablation catheter that may be used in conjunction with the endoscope of FIG. 2A.

FIG. 3 shows a schematic representation of RF ablation catheter (114) that may be used in conjunction with endoscope (112) of FIGS. 2A-2B. As shown, RF ablation catheter (114) includes a shaft (136) that includes proximal and distal ends (138, 140), with distal end (140) disposed opposite proximal end (138). RF ablation catheter (114) is configured to pass through working channel (126) of endoscope (112). RF ablation catheter (114) includes at least one electrode (with first and second electrodes (142, 144) being shown) in electrical communication with RF energy source (116). First and second electrodes (142, 144) are disposed on distal end (140) of RF ablation catheter (114) and are configured to transmit RF energy obtained from RF energy source (116) to tissue (e.g. tissue located in a posterior nasal region (PNR)). As shown, first electrode (142) is electrically coupled with RF energy source (116) using first wire (146), and second electrode (144) is electrically coupled with RF energy source (116) using second wire (148). Bipolar energy may travel through tissue that is positioned between electrodes (142, 144).

While application of bipolar RF energy using first and second electrodes (142, 144) is shown and described, it is also envisioned that RF ablation catheter (114) may utilize monopolar RF energy. For example, for monopolar RF energy, a single electrode may be disposed at distal end (140) of RF ablation catheter (114) to apply the RF energy with a ground pad (not shown) contacting the skin of patient (P). RF ablation catheter (114) is configured to be removably coupled with RF energy source (116). For example, a coupling (150) may couple proximal end (138) of RF ablation catheter (114) with RF energy source (116). However, coupling (150) may instead be positioned on another portion of RF ablation catheter (114) that remains outside of patient (P).

As shown, distal end (140) of RF ablation catheter (114) may include a position sensor (152) that communicates with control (118) using a wired or wireless connection. Position sensor (152) may facilitate tracking of the three-dimensional position of distal end (140) in real time. Particularly, position sensor (152) may verify that RF ablation catheter (114) is properly positioned in posterior nasal region (PNR). However, position sensors (135, 152) and/or IGS navigation system (10) are merely optional and are not required.

C. Exemplary Method of Use

Figure 4A:
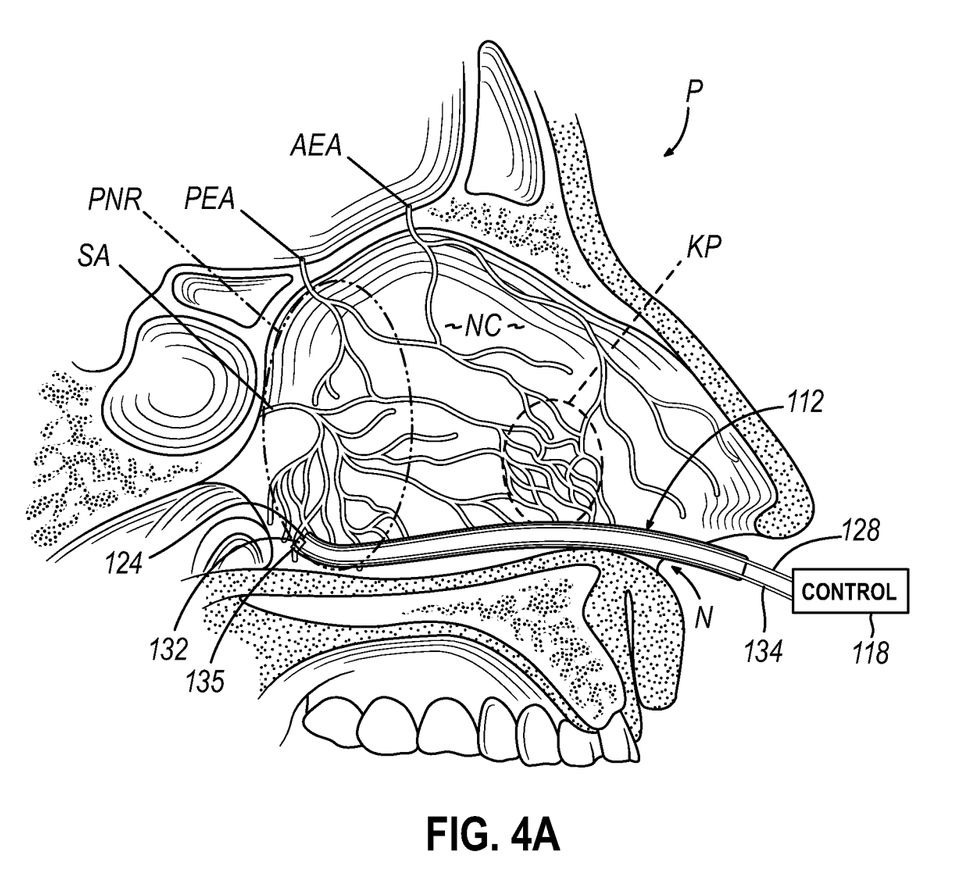
FIG. 4A depicts a sectional view of the distal end of the endoscope being inserted through the nostril and into the nasal cavity of the patient.

FIGS. 4A-4E show an exemplary method of treating epistaxis. For example, this exemplary method may be used to treat severe epistaxis, also known as acute epistaxis. As shown in FIG. 4A, distal end (124) of endoscope (112) is inserted through nostril (N) and into nasal cavity (NC) of patient (P). Endoscope (112) allows a user (e.g. surgeon) to more easily reach around the anatomical structures that would otherwise be in the way of a rigid endoscope. Those in-the-way anatomical structures (e.g. turbinate structures) are omitted in FIG. 4A, due to the plane at which the cross-section is taken. Particularly, FIG. 4A shows endoscope (112) entering nostril (N) at a generally horizontal orientation, with the entry point close to the tip of the nostril (N), with the distal end (124) bent upwardly to reach Stamm's S-point region (S). Distal end (124) of endoscope (112) may be steered into and through nasal cavity (NC) using pull wire (128). Once inserted into the nasal cavity (NC), endoscope (112) is advanced further using control (118) to the desired position within posterior nasal region (PNR), which may be the site of posterior epistaxis. As described previously with reference to FIGS. 2A-2B, control (118) is located outside of patient (P) to enable the user to steer endoscope (112) while within nasal cavity (NC) of patient (P). More specifically, endoscope (112) may be guided to Stamm's S-point region (S) of posterior nasal region using control (118). Also shown within nasal cavity (NC) are Kiesselbach's plexus (KP), anterior ethmoidal artery (AEA), posterior ethmoidal artery (PEA), and sphenopalatine artery (SA).

Figure 4B:
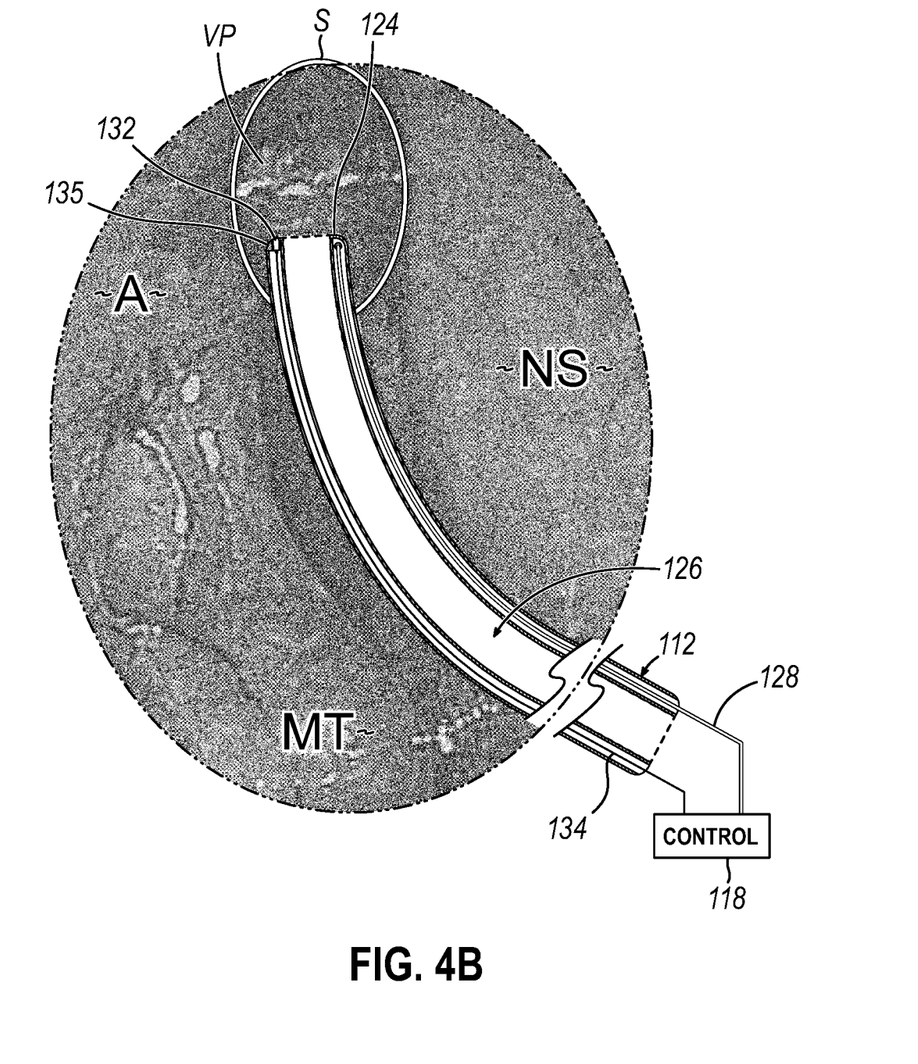
FIG. 4B depicts an enlarged perspective view of the posterior nasal region of the nasal cavity with the distal end of the endoscope positioned using the control to a position adjacent a vascular pedicle in Stamm's S-point region and between the axilla of the middle turbinate and the nasal septum.

FIG. 4B shows an enlarged view of posterior nasal region (PNR) of nasal cavity (NC) with distal end (124) of endoscope (112) positioned using control (118) to a desired position. As shown, the desired position is adjacent a vascular pedicle (VP) in Stamm's S-point region (S) and between axilla (A) of middle turbinate (MT) and nasal septum (NS). This positioning allows for first and second electrodes (142, 144) to ablate at least a portion of Stamm's S-point region (S) of posterior nasal region (PNR) using RF energy. As described above with reference to FIGS. 2A-2B, camera (132) may be configured to provide images to the display screen to ensure RF ablation catheter (114) is properly positioned in posterior nasal region (PNR) prior to ablating tissue.

Figure 4C:
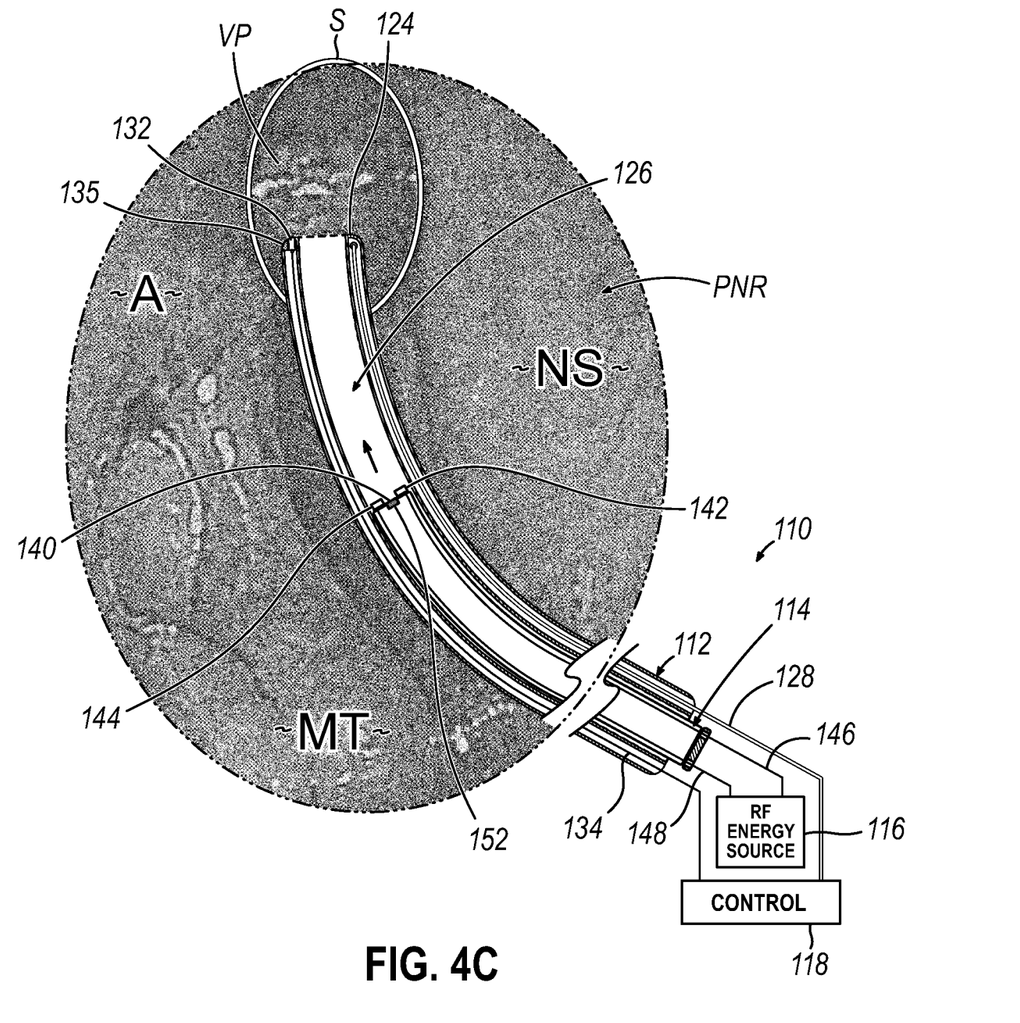
FIG. 4C depicts the enlarged perspective view of the posterior nasal region of the nasal cavity of FIG. 4B, but with the distal end of the RF ablation catheter being advanced distally through the working channel of the endoscope.

FIG. 4C shows the enlarged view of the posterior nasal region (PNR) of FIG. 4B, but with distal end (140) of RF ablation catheter (114) being advanced distally through working channel (126) of endoscope (112), with endoscope (112) being shown schematically. Distal end (124) of endoscope (112) may be advanced to the desired position (e.g., into posterior nasal region) prior to advancing RF ablation catheter (114) through working channel (126) of endoscope (112). RF ablation catheter (114) may be advanced both through working channel (126) and through distal end (124) of endoscope (112) in posterior nasal region (PNR). As previously described with reference to FIGS. 2A-3, distal end (124) of endoscope (112) may include position sensor (135) and/or distal end (140) of RF ablation catheter (114) may include position sensor (152). Position sensors (135, 152) may verify that endoscope (112) and RF ablation catheter (114) is properly positioned in posterior nasal region (PNR). However, use of position sensors (135, 152) and/or IGS navigation system (10) are merely optional and are not required.

Figure 4D:
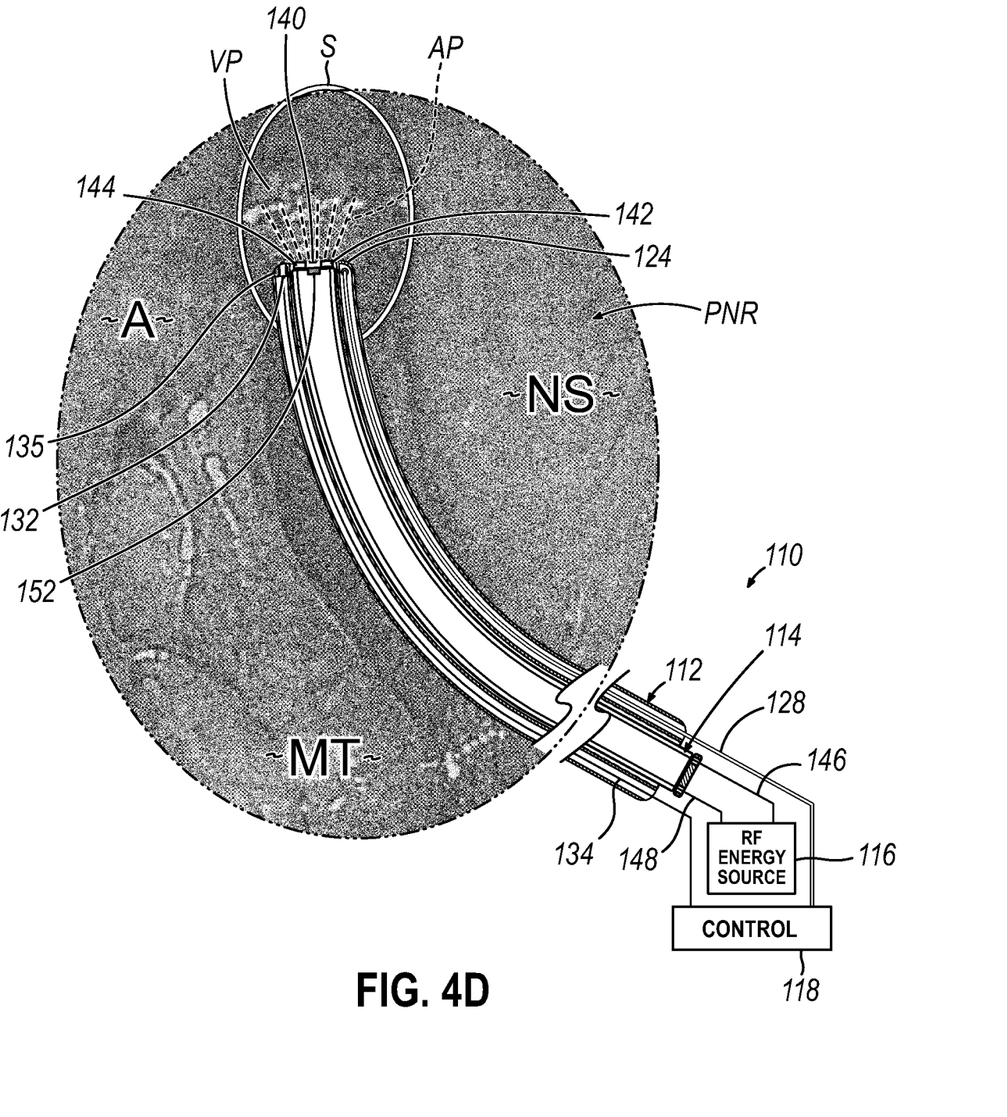
FIG. 4D depicts the enlarged perspective view of the posterior nasal region of the nasal cavity of FIG. 4C, but with the distal end of the RF ablation catheter positioned flush with the distal end of the endoscope, and first and second electrodes of the RF ablation catheter ablating the vascular pedicle in Stamm's S-point region.

FIG. 4D shows an ablated portion (AP) of tissue being ablated in posterior nasal region (PNR) of nasal cavity (NC) using RF energy transmitted by RF ablation catheter (114). As shown, distal end (140) of RF ablation catheter (114) is positioned flush with distal end (124) of endoscope (112). Alternatively, while not shown, distal end (140) of RF ablation catheter (114) may be positioned proximally or distally relative to distal end (124) of endoscope (112). First and second electrodes (142, 144) use RF energy transmitted from RF energy source (116) to ablate tissue. As shown, first and second electrodes (142, 144) ablate vascular pedicle (VP) in Stamm's S-point region (S) of posterior nasal region (PNR) to treat severe epistaxis. It is envisioned that RF energy source (116) may be coupled in any manner sufficient to transmit RF energy to first and second electrodes (142, 144) at any time prior to ablating the tissue. Camera (132) provides images to display screen, such that the user may ensure the desired area (e.g. ablated portion (AP) of vascular pedicle (VP) in Stamm's S-point region (S)) is properly and sufficiently ablated.

Figure 4E:
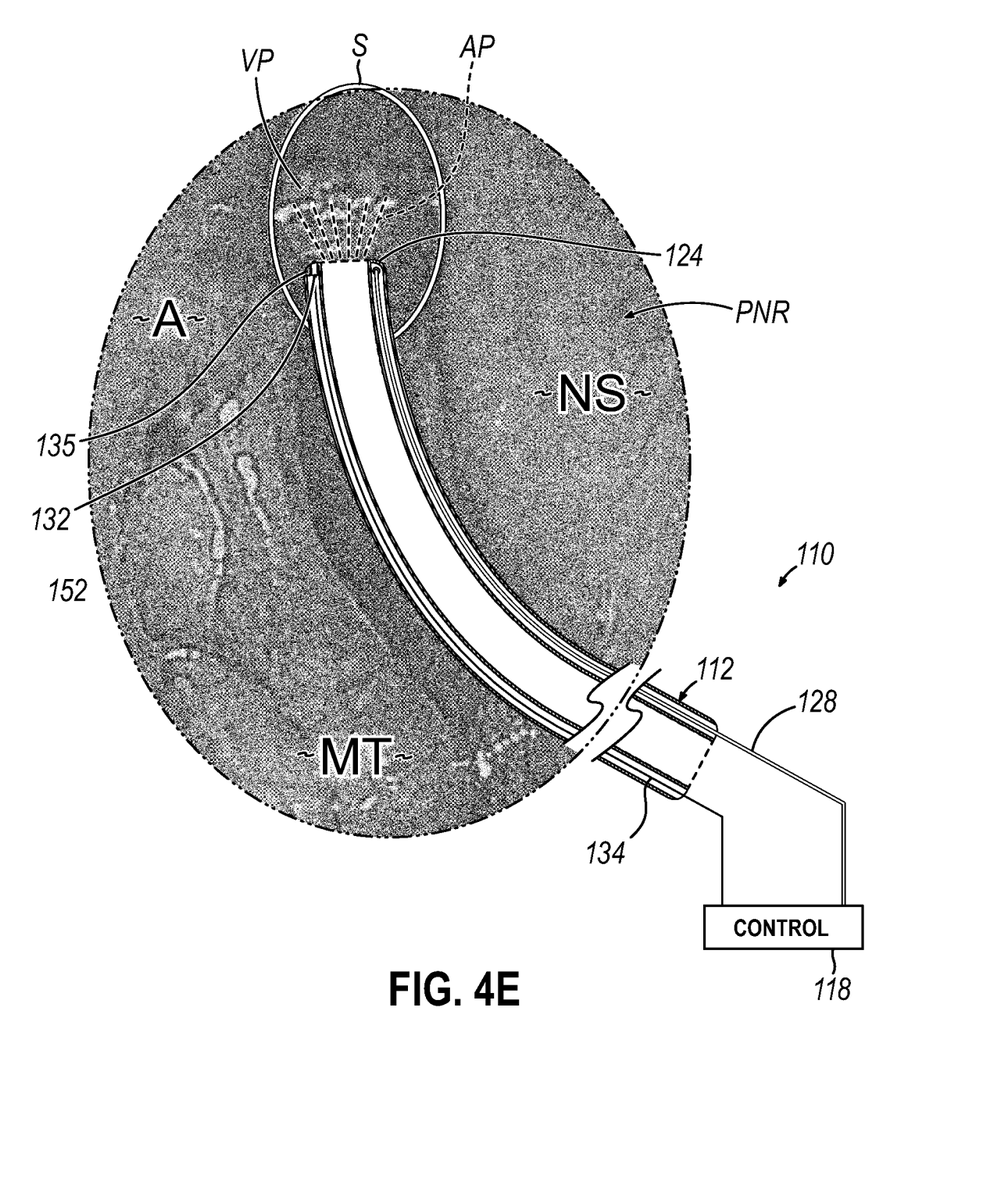
FIG. 4E depicts the enlarged perspective view of the posterior nasal region of the nasal cavity of FIG. 4D, but with the RF ablation catheter retracted proximally after ablation of the vascular pedicle in Stamm's S-point region.
Figure 4F:
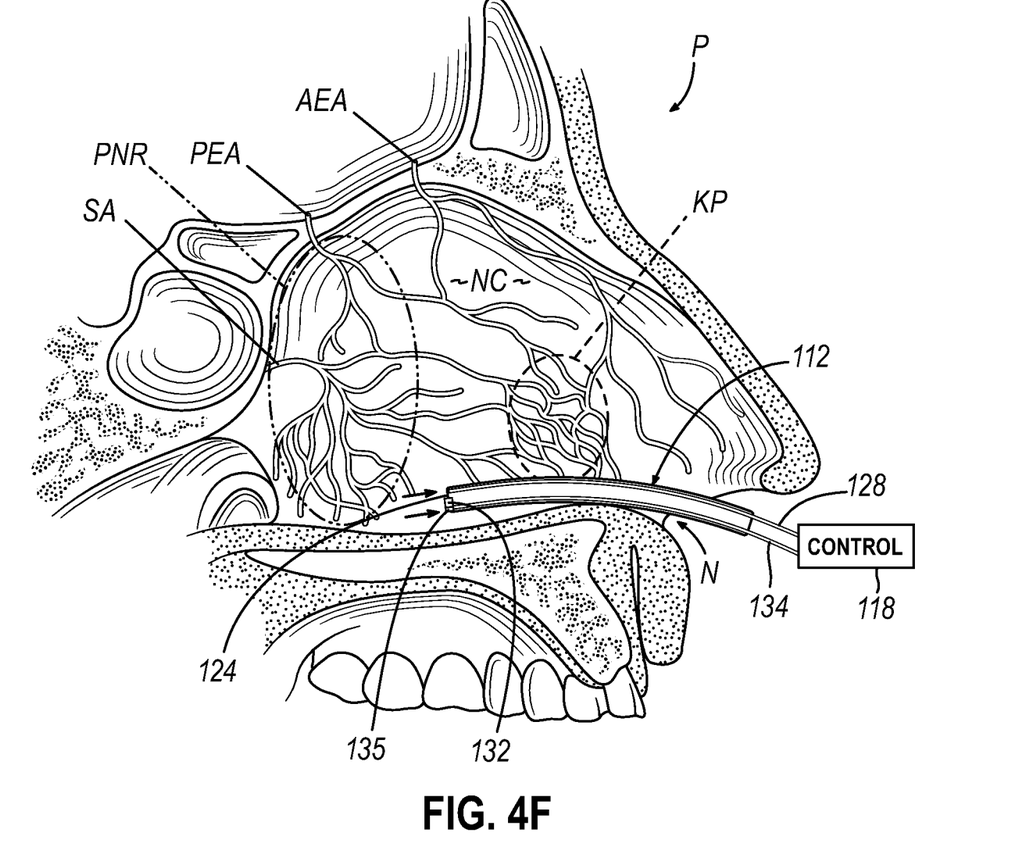
FIG. 4F depicts a sectional view of the distal end of the endoscope being retracted proximally from the nasal cavity of the patient.

FIG. 4E shows an enlarged view of posterior nasal region (PNR) of nasal cavity (NC) of FIG. 4D, but with RF ablation catheter (114) retracted proximally after ablation of vascular pedicle (VP) in Stamm's S-point region (S). FIG. 4F shows endoscope (112) being retracted proximally from nasal cavity (NC). While not shown, it is also envisioned that endoscope (112) and RF ablation catheter (114) may be retracted together as a unit.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor-in-interest to the inventors. If any claims are presented in this application or in subsequent filings related to this application that include additional features beyond those referred to below, those additional features shall not be presumed to have been added for any reason relating to patentability.

Example 1

A method of treating epistaxis, the method comprising: (a) inserting a distal end of an endoscope into a nasal cavity of a patient, wherein at least the distal end of the endoscope includes a working channel; (b) advancing a distal end of an RF ablation catheter through the working channel of the endoscope; and (c) ablating tissue in a posterior nasal region of the nasal cavity using RF energy transmitted by the RF ablation catheter.

Example 2

The method of Example 1, wherein the endoscope is a steerable endoscope that is coupled with a control, wherein the method further comprises steering the steerable endoscope within the nasal cavity of the patient using the control that is located outside of the patient.

Example 3

The method of Example 2, further comprising steering the steerable endoscope to Stamm's S-point region of the posterior nasal region using the control, wherein ablating the tissue further includes ablating at least a portion of the Stamm's S-point region of the posterior nasal region using RF energy transmitted by the RF ablation catheter.

Example 4

The method of any one or more of Examples 2 through 3, wherein the steerable endoscope includes a camera at the distal end of the steerable endoscope, wherein the camera communicates with the control, wherein prior to ablating the tissue in the posterior nasal region, the method further includes verifying the RF ablation catheter is properly positioned in the posterior nasal region of the nasal cavity using the camera.

Example 5

The method of any one or more of Examples 2 through 3, wherein the steerable endoscope includes a camera at the distal end of the steerable endoscope, wherein the camera produces images and communicates with a navigational system that displays images obtained by the camera of the nasal cavity on a display screen, wherein prior to ablating the tissue in the posterior nasal region, the method further includes verifying the RF ablation catheter is properly positioned in the posterior nasal region of the nasal cavity using the images provided by the camera on the display screen.

Example 6

The method of any one or more of Examples 2 through 5, wherein the steerable endoscope includes a shaft with the working channel extending completely therethrough, wherein steering the steerable endoscope further includes bending a flexible portion of the shaft away from a longitudinal axis of the shaft.

Example 7

The method of Example 6, wherein the steerable endoscope includes at least one pull wire extending through the shaft, wherein steering the steerable endoscope further includes steering the distal end of the steerable endoscope into the nasal cavity using the at least one pull wire.

Example 8

The method of Example 7, wherein steering the distal end of the steerable endoscope further includes proximally retracting the at least one pull wire to articulate the distal end of the steerable endoscope.

Example 9

The method of any one or more of Examples 2 through 8, further comprising advancing the distal end of the steerable endoscope into the posterior nasal region prior to advancing the RF ablation catheter through the working channel of the steerable endoscope.

Example 10

The method of any one or more of Examples 1 through 9, wherein advancing the RF ablation catheter further includes advancing the RF ablation catheter both through the working channel and through the distal end of the endoscope in the posterior nasal region.

Example 11

The method of any one or more of Examples 1 through 10, wherein the RF ablation catheter includes first and second electrodes disposed at the distal end of the RF ablation catheter, wherein the method further includes ablating the tissue in a posterior nasal region using the first and second electrodes.

Example 12

The method of Example 11, wherein the RF ablation catheter includes a coupling at a proximal end of the RF ablation catheter, wherein the method further comprises coupling an RF energy source to the coupling of the RF ablation catheter to provide RF energy to the first and second electrodes to ablate the tissue in the posterior nasal region of the nasal cavity.

Example 13

The method of any one or more of Examples 1 through 12, wherein ablating the tissue in the posterior nasal region further includes ablating a vascular pedicle in the posterior nasal region using RF energy transmitted by the RF ablation catheter.

Example 14

The method of Example 13, wherein ablating the vascular pedicle further includes ablating the vascular pedicle in Stamm's S-point region of the posterior nasal region using RF energy transmitted by the RF ablation catheter

Example 15

The method of any one or more of Examples 1 through 14, wherein the method is used to treat severe epistaxis.

Example 16

A method of treating severe epistaxis, the method comprising: (a) inserting a distal end of a steerable endoscope into a nasal cavity of a patient, wherein at least the distal end of the steerable endoscope includes a working channel; (b) advancing a distal end of an RF ablation catheter through the working channel of the steerable endoscope; (c) verifying using a camera coupled with the distal end of the steerable endoscope that the RF ablation catheter is positioned adjacent a vascular pedicle in Stamm's S-point region in a posterior nasal region of the nasal cavity; and (d) ablating the vascular pedicle in the Stamm's S-point region of the nasal cavity using RF energy transmitted by an electrode of the RF ablation catheter.

Example 17

The method of Example 16, further comprising visualizing the posterior nasal region including the Stamm's S-point region using the steerable endoscope.

Example 18

The method of any one or more of Examples 16 through 17, wherein advancing the RF ablation catheter further includes advancing the RF ablation catheter both through the working channel and through the distal end of the steerable endoscope such that the RF ablation catheter is positioned adjacent the vascular pedicle in the Stamm's S-point region.

Example 19

A system comprising: (a) an RF energy source configured to provide radiofrequency energy; (b) a steerable endoscope that includes a shaft defining a longitudinal axis, wherein the shaft includes: (i) a distal end that is configured to fit through a human nostril into a nasal cavity, (ii) a working channel extending at least though the distal end, and (iii) at least one pull wire; and (c) an RF ablation catheter configured to pass through the working channel of the steerable endoscope, wherein the RF ablation catheter includes at least one electrode in electrical communication with the RF energy source, wherein the electrode is configured to transmit RF energy obtained from the RF energy source to tissue located in a posterior nasal region of the nasal cavity.

Example 20

The system of Example 19, wherein the system further comprises a control that includes a display screen, wherein the steerable endoscope includes a camera at the distal end of the steerable endo scope, wherein the camera is configured to produce images which the control displays on the display screen such that the RF ablation catheter is properly positioned in the posterior nasal region of the nasal cavity using the images provided by the camera on the display screen.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc., described herein may be combined with any one or more of the other teachings, expressions, embodiments, examples, etc., that are described herein. The above-described teachings, expressions, embodiments, examples, etc., should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and, if necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A method of treating epistaxis, the method comprising:
   (a) inserting a distal end of an endoscope into a nasal cavity of a patient, wherein at least the distal end of the endoscope includes a working channel and a distal tip, wherein the endoscope defines a tubular perimeter;
   (b) advancing a distal end of a radiofrequency (RF) ablation catheter through the working channel of the endoscope, wherein the distal end of the RF ablation catheter includes a distal tip;
   (c) arresting advancement of the RF ablation catheter while the distal tip of the RF ablation catheter is positioned at the distal tip of the endoscope and while the distal tip of the RF ablation catheter is radially positioned within the tubular perimeter defined by the endoscope; and
   (d) ablating tissue in a posterior nasal region of the nasal cavity using RF energy transmitted by the RF ablation catheter while the distal tip of the RF ablation catheter is positioned at the distal tip of the endoscope and while the distal tip of the RF ablation catheter is radially positioned within the tubular perimeter defined by the endoscope.

2. The method of claim 1, wherein the endoscope is a steerable endoscope that is coupled with a control, wherein the method further comprises steering the steerable endoscope within the nasal cavity of the patient using the control that is located outside of the patient.

3. The method of claim 2, further comprising steering the steerable endoscope to Stamm's S-point region of the posterior nasal region using the control, wherein ablating the tissue further includes ablating at least a portion of the Stamm's S-point region of the posterior nasal region using RF energy transmitted by the RF ablation catheter.

4. The method of claim 2, wherein the steerable endoscope includes a camera at the distal end of the steerable endoscope, wherein the camera communicates with the control, wherein prior to ablating the tissue in the posterior nasal region, the method further includes verifying the RF ablation catheter is properly positioned in the posterior nasal region of the nasal cavity using the camera.

5. The method of claim 2, wherein the steerable endoscope includes a camera at the distal end of the steerable endoscope, wherein the camera produces images and communicates with a navigational system that displays images obtained by the camera of the nasal cavity on a display screen, wherein prior to ablating the tissue in the posterior nasal region the method further includes verifying the RF ablation catheter is properly positioned in the posterior nasal region of the nasal cavity using the images provided by the camera on the display screen.

6. The method of claim 2, wherein the steerable endoscope includes a shaft with the working channel extending completely therethrough, wherein steering the steerable endoscope further includes bending a flexible portion of the shaft away from a longitudinal axis of the shaft.

7. The method of claim 6, wherein the steerable endoscope includes at least one pull wire extending through the shaft, wherein steering the steerable endoscope further includes steering the distal end of the steerable endoscope into the nasal cavity using the at least one pull wire.

8. The method of claim 7, wherein steering the distal end of the steerable endoscope further includes proximally retracting the at least one pull wire to articulate the distal end of the steerable endoscope.

9. The method of claim 2, further comprising advancing the distal end of the steerable endoscope into the posterior nasal region prior to advancing the RF ablation catheter through the working channel of the steerable endoscope.

10. The method of claim 1, wherein advancing the RF ablation catheter further includes advancing the RF ablation catheter both through the working channel and through the distal end of the endoscope in the posterior nasal region.

11. The method of claim 1, wherein the RF ablation catheter includes first and second electrodes disposed at the distal end of the RF ablation catheter, wherein the method further includes ablating the tissue in a posterior nasal region using the first and second electrodes.

12. The method of claim 11, wherein the RF ablation catheter includes a coupling at a proximal end of the RF ablation catheter, wherein the method further comprises coupling an RF energy source to the coupling of the RF ablation catheter to provide RF energy to the first and second electrodes to ablate the tissue in the posterior nasal region of the nasal cavity.

13. The method of claim 1, wherein ablating the tissue in the posterior nasal region further includes ablating a vascular pedicle in the posterior nasal region using RF energy transmitted by the RF ablation catheter.

14. The method of claim 13, wherein ablating the vascular pedicle further includes ablating the vascular pedicle in Stamm's S-point region of the posterior nasal region using RF energy transmitted by the RF ablation catheter.

15. The method of claim 1, wherein the method is used to treat severe epistaxis.

16. A method of treating posterior epistaxis, the method comprising:
(a) inserting a distal end of a steerable endoscope into a nasal cavity of a patient, wherein at least the distal end of the steerable endoscope includes a working channel and a distal tip;
(b) inserting a distal end of a radiofrequency (RF) ablation catheter into the working channel of the steerable endoscope, wherein the distal end of the RF ablation catheter includes a distal tip having a position sensor;
(c) advancing the RF ablation catheter distally along the working channel of the steerable endoscope;
(d) arresting advancement of the RF ablation catheter once the position sensor of the distal tip indicates that the RF ablation catheter is positioned flush with the distal tip of the steerable endoscope;
(e) verifying using a camera coupled with the distal end of the steerable endoscope that the RF ablation catheter is positioned adjacent a vascular pedicle in Stamm's S-point region in a posterior nasal region of the nasal cavity; and
(f) ablating the vascular pedicle in the Stamm's S-point region of the nasal cavity using RF energy transmitted by an electrode of the RF ablation catheter while the distal tip of the RF ablation catheter is positioned flush with the distal tip of the steerable endoscope.

17. The method of claim 16, further comprising visualizing the posterior nasal region including the Stamm's S-point region using the steerable endoscope.

18. The method of claim 16, wherein advancing the RF ablation catheter further includes advancing the RF ablation catheter both through the working channel and to the distal end of the steerable endoscope such that the RF ablation catheter is positioned adjacent the vascular pedicle in the Stamm's S-point region.

* * * * *